(12) United States Patent
Yang et al.

(10) Patent No.: US 10,676,497 B2
(45) Date of Patent: Jun. 9, 2020

(54) TYPE OF TAXANE COMPOUND, PREPARATION METHOD AND APPLICATION THEREOF

(71) Applicants: CHANGZHOU FANGYUAN PHARMACEUTICAL CO., LTD, Changzhou (CN); INNER MONGOLIA PUYIN PHARMACEUTICAL CO., LTD., Chifeng (CN)

(72) Inventors: Daria Yang, Changzhou (CN); Huijuan Wang, Changzhou (CN)

(73) Assignees: CHANGZHOU FANGYUAN PHARMACEUTICAL CO., LTD., Changzhou (CN); INNER MONGOLIA PUYIN PHARMACEUTICAL CO., LTD., Chifeng (CN)

( * ) Notice: Subject to any disclaimer, the term of this patent is extended or adjusted under 35 U.S.C. 154(b) by 0 days.

(21) Appl. No.: 16/310,403

(22) PCT Filed: Nov. 14, 2016

(86) PCT No.: PCT/CN2016/105692
§ 371 (c)(1),
(2) Date: Dec. 14, 2018

(87) PCT Pub. No.: WO2017/215188
PCT Pub. Date: Dec. 21, 2017

(65) Prior Publication Data
US 2019/0256545 A1    Aug. 22, 2019

(30) Foreign Application Priority Data
Jun. 15, 2016 (CN) .......................... 2016 1 0426133

(51) Int. Cl.
| | | |
|---|---|---|
| *C07H 19/06* | (2006.01) |
| *C07D 305/14* | (2006.01) |
| *C07D 405/14* | (2006.01) |
| *A61P 35/02* | (2006.01) |
| *C07H 1/00* | (2006.01) |
| *A61P 1/00* | (2006.01) |
| *A61P 35/00* | (2006.01) |

(52) U.S. Cl.
CPC ................ *C07H 19/06* (2013.01); *A61P 1/00* (2018.01); *A61P 35/00* (2018.01); *A61P 35/02* (2018.01); *C07D 305/14* (2013.01); *C07D 405/14* (2013.01); *C07H 1/00* (2013.01); *Y02P 20/55* (2015.11)

(58) Field of Classification Search
None
See application file for complete search history.

(56) References Cited

FOREIGN PATENT DOCUMENTS

| | | | |
|---|---|---|---|
| CN | 102264396 A | 11/2011 | |
| WO | 2012004005 A1 | 1/2012 | |
| WO | WO-2012004005 A1 * | 1/2012 | ............. A61K 47/61 |

OTHER PUBLICATIONS

The World Intellectual Property Organization (WIPO) International Search Report for PCT/CN2016/105692 dated Mar. 20, 2017 6 Pages.

* cited by examiner

*Primary Examiner* — Traviss C McIntosh, III
(74) *Attorney, Agent, or Firm* — Anova Law Group, PLLC

(57) ABSTRACT

The present disclosure provides a taxane compound and a preparation method and application thereof. The preparation method includes: protecting two hydroxyl groups in gemcitabine, conducting a condensation reaction between the protected gemcitabine and alkyl chloroformate, and removing of hydroxyl protecting groups to obtain an intermediate G1; protecting a first hydroxyl group of the intermediate G1, and then protecting the other one of the hydroxyl groups, and removing a protecting group of the first hydroxyl group to obtain an intermediate G2; reacting 7,10-di-troc-docetaxel with dianhydride to obtain an intermediate D1; conducting a condensation reaction between the intermediate D1 and the intermediate G2 to obtain an intermediate D2; and subjecting the intermediate D2 to hydroxyl deprotection to obtain a target product comprising the disclosed taxane compound.

10 Claims, 7 Drawing Sheets

TYPE OF TAXANE COMPOUND, PREPARATION METHOD AND APPLICATION THEREOF

CROSS-REFERENCES TO RELATED APPLICATIONS

This application is a national phase entry under 35 U.S.C. § 371 of International Application No. PCT/CN2016/105692, filed on Nov. 14, 2016, which claims the priority to Chinese Patent Application No. 201610426133.4, filed with the State Intellectual Property Office of P. R. China on Jun. 15, 2016, the entire contents of all of which are incorporated herein by reference.

FIELD OF THE DISCLOSURE

The present disclosure relates to a new type of taxane compound, and a preparation method of the taxane compound, and application of the taxane compound.

BACKGROUND

Most existing taxane compounds have deficiencies such as high toxicity and low anti-tumor activity, especially poor inhibitory effects on leukemia and solid tumors such as gastrointestinal cancers, lung cancers, and breast cancers.

SUMMARY OF THE DISCLOSURE

An objective of the present disclosure is to solve the defects existing in the prior art, to provide a new type of taxane compound with low toxicity and high anti-tumor activity, which exhibits good inhibition rate for leukemias and solid tumors such as gastrointestinal cancers, lung cancers, and breast cancers, and to provide a preparation method and application of the taxane compound.

The technical solution for achieving the above objective of the present disclosure is: a new type of taxane compound having a structure as shown in formula (I):

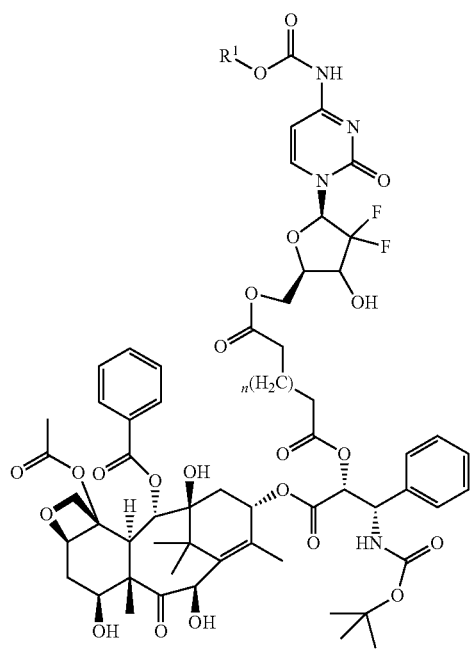

In formula (I), $R^1$ is a $C_1$-$C_6$ alkyl or substituted alkyl, preferably is ethyl, n-butyl or n-hexyl, and more preferably is n-butyl.

n is 0 to 6, preferably is 0 to 2, and more preferably is 1.

The aforementioned preparation method of the new type of taxane compound has the following steps:

S1: protecting two hydroxyl groups in gemcitabine, and then conducting a condensation reaction between the protected gemcitabine and alkyl chloroformate, followed by removal of hydroxy protecting groups to obtain an intermediate G1;

S2: protecting first one of the hydroxyl groups of the intermediate G1 prepared by step S1, and then protecting the other one of the hydroxyl groups, followed by removal of the first one of the hydroxyl protecting groups to obtain an intermediate G2;

S3: reacting 7,10-di-troc-docetaxel with dianhydride to obtain an intermediate D1;

S4: conducting a condensation reaction between the intermediate D1 prepared by step S3 and the intermediate G2 prepared by step S2 to obtain an intermediate D2; and S5: subjecting the intermediate D2 prepared by step S4 to hydroxyl deprotection to obtain a target product.

The hydroxyl protecting agent used in the aforementioned step S1 is hexamethyldisilazane, hexamethyldisiloxane, trimethylchlorosilane or trimethyliodosilane, and preferably hexamethyldisilazane.

The alkyl chloroformate described in the above step S1 is one of methyl chloroformate, ethyl chloroformate, n-propyl chloroformate, isopropyl chloroformate, n-butyl chloroformate, n-amyl chloroformate, n-hexyl chloroformate, preferably ethyl chloroformate, n-butyl chloroformate or n-hexyl chloroformate, and more preferably n-butyl chloroformate.

The protecting agent used for protection of the first hydroxyl group in the aforementioned step S2 is tert-butyldimethylchlorosilane, isopropyldimethylchlorosilane, ethyldimethylchlorosilane or trimethylchlorosilane, and preferably tert-butyldimethylchlorosilane.

The protecting agent used for protection of the second hydroxyl group in the aforementioned step S2 is 2,2,2-trichloroethyl chloroformate.

The dianhydride used in the aforementioned step S3 is succinic anhydride, glutaric anhydride or adipic anhydride, and preferably glutaric anhydride.

The reagent used in the condensation reaction in the aforementioned step S4 is N-(3-dimethylaminopropyl)-N'-ethylcarbodiimide hydrochloride (EDCI), 1-(3-dimethylaminopropyl)-3-ethylcarbodiimide hydrochloride (EDC), dicyclohexyl carbodiimide (DCC) or N,N-diisopropyl carbodiimide (DIC), preferably N-(3-dimethylaminopropyl)-N'-ethylcarbodiimide hydrochloride or 1-(3-dimethylaminopropyl)-3-ethylcarbodiimide hydrochloride, and more preferably N-(3-dimethylaminopropyl)-N'-ethylcarbodiimide hydrochloride.

The condensation reaction in the aforementioned step S4 is preferably carried out in the presence of 4-dimethylaminopyridine.

The hydroxyl deprotection of the aforementioned step S5 is carried out in the presence of zinc powder and sodium acetate.

The aforementioned new type of taxane compound can be applied in preparation of an anti-tumor drug.

The tumor is a blood tumor or a malignant solid tumor; specifically, the aforementioned tumor includes a colon cancer, a rectal cancer, a gastric cancer, a lung cancer, a breast cancer, a prostate cancer, a pancreatic cancer, a liver cancer, an esophageal cancer, a brain tumor, an ovarian cancer, an uterine cancer, a kidney cancer, a head and neck cancer, a skin cancer, a bladder cancer, a vulvar cancer, a testicular tumor, a villus cancer, a germ cell tumor, a malignant lymphoma, a leukemia and a multiple myeloma; and preferably includes a colon cancer, a rectal cancer, a gastric cancer, a lung cancer, a breast cancer and a leukemia.

A pharmaceutical composition, consisting of the aforementioned new type of taxane compound as an active component and one or more pharmaceutically acceptable carriers/excipients.

The dosage form of the aforementioned pharmaceutical composition is an injection dosage form or an oral dosage form, where the injection dosage form is a solution injection, a suspension injection, an emulsion injection, or sterile powder for injection; and the oral dosage form is a tablet, a powder, a granule, a capsule, a pellet preparation, a solution, a suspension, an emulsion, a syrup or an elixir.

The advantageous effects of the present disclosure include: the new type of taxane compound of the present disclosure has low toxicity (the maximum tolerated dose, i.e., MTD, is only 250 mg/kg) and high anti-tumor activity, and particularly has a good inhibition rate for leukemias and solid tumors such as gastrointestinal cancers, lung cancers, and breast cancers (with a tumor growth inhibition rate, i.e., TGI, of colon cancer up to 85.69%).

DETAILED DESCRIPTION

Example 1

Figure 1:
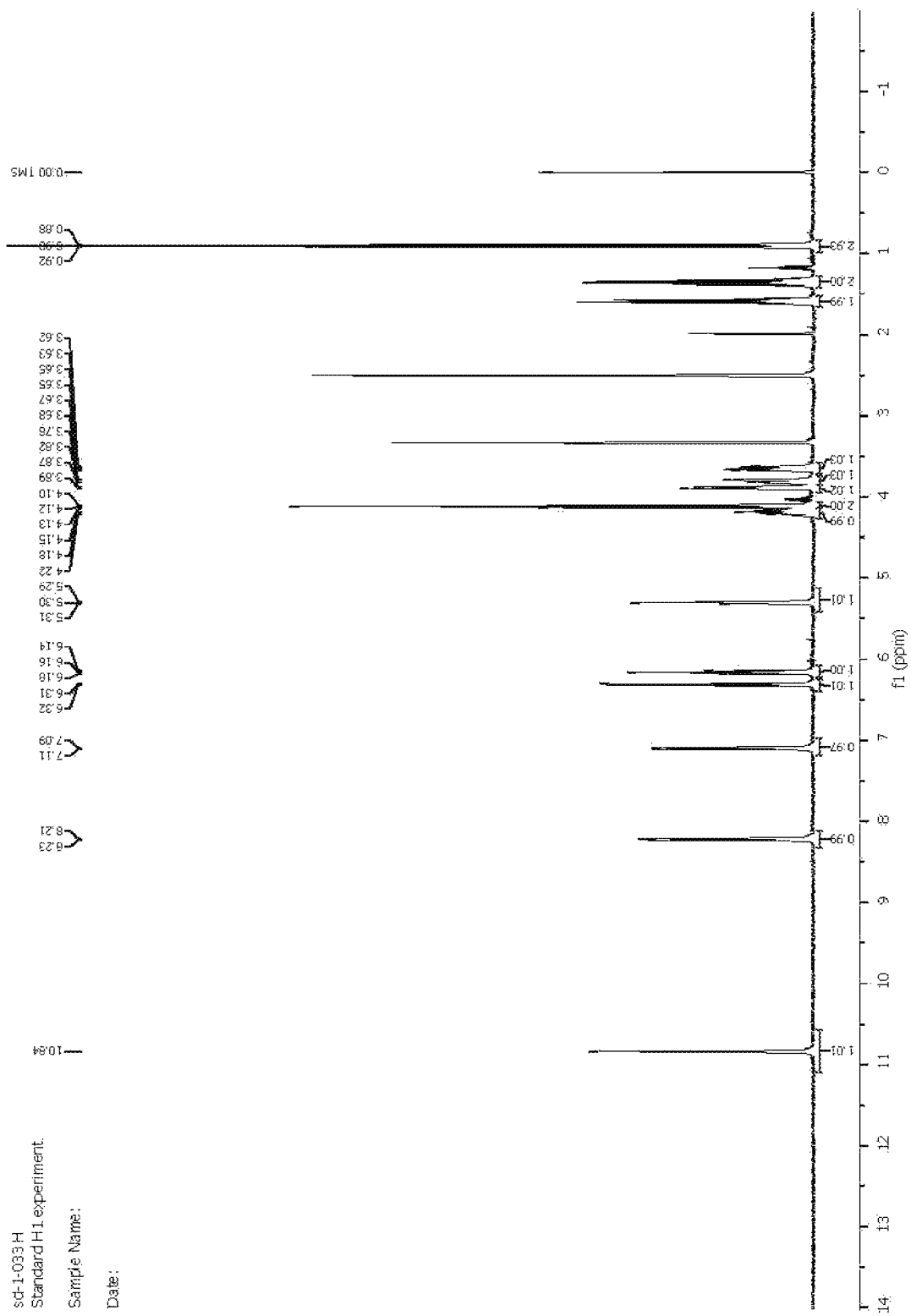
FIG. 1 is a $^1$H-NMR spectrogram of the intermediate G1.

The new type of taxane compound Z1 of this example has the following structural formula:

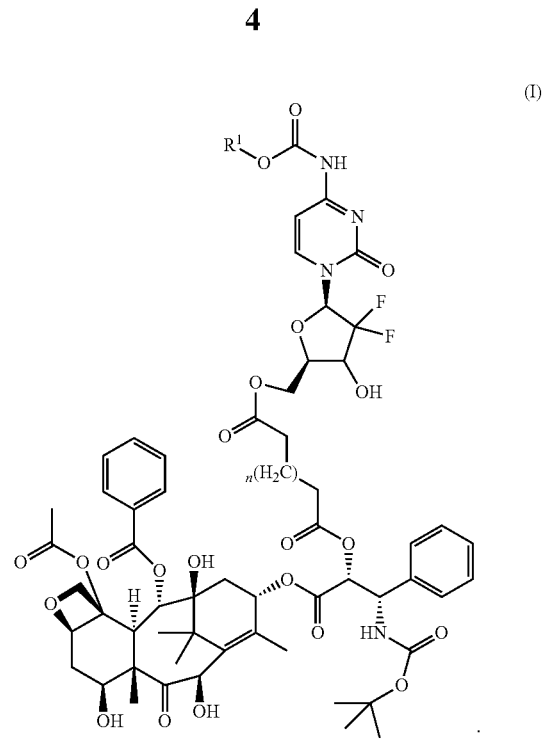

(I)

A preparation method of the new type of taxane compound Z1 has the following steps:

S1: the intermediate G1 was prepared, with a synthesis route as follows:

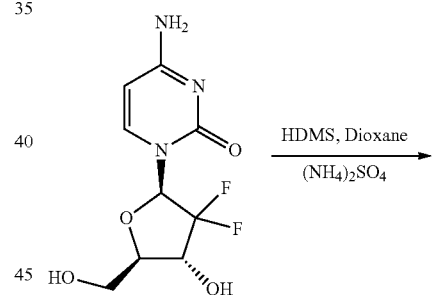

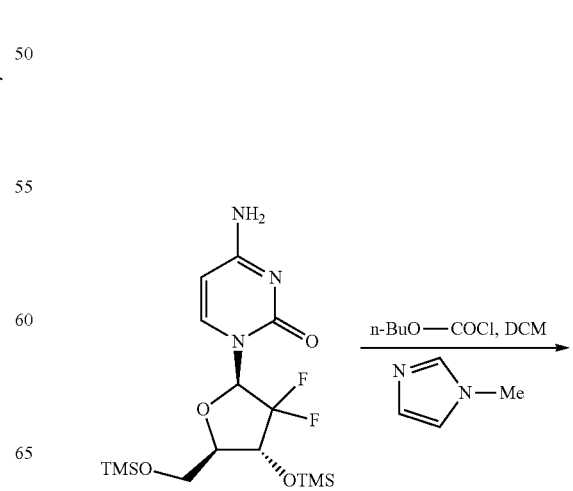

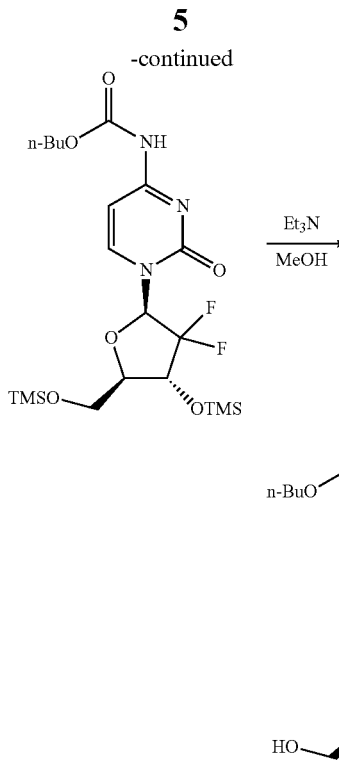

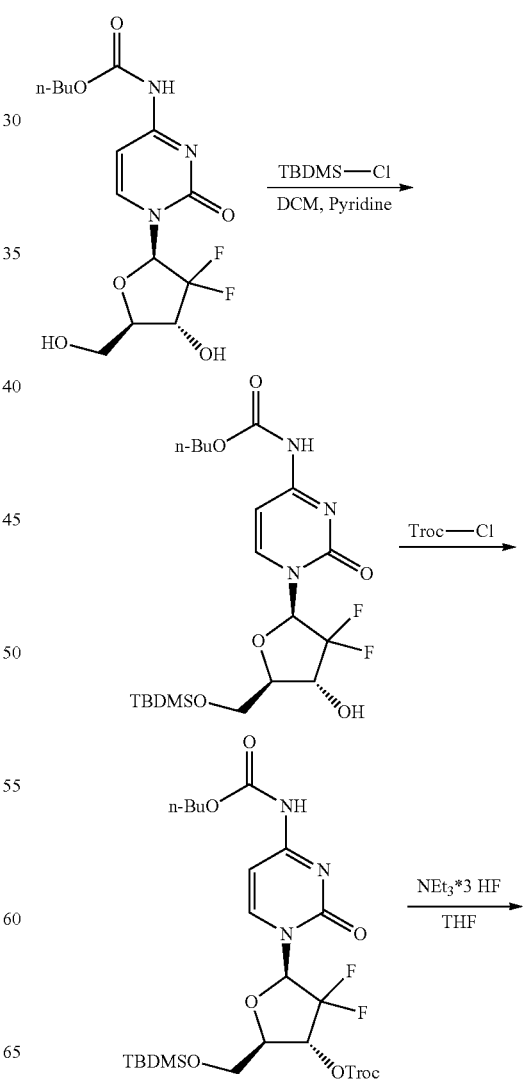

The specific method is as follows:

S11: Into a one-liter round-bottom flask, 30 g of gemcitabine (0.114 mol), 143 mL of hexamethyldisilazane (0.68 mol, 6 equiv), 0.569 g of ammonium sulfate (4 mmol, 0.038 equiv) and 143 mL of dioxane were added to obtain a mixture; and then the mixture was placed in an oil bath at 130° C. and refluxed for 1.5 h until no more ammonia was produced.

After evaporation of the volatiles, firstly the semi-crystalline solid was vacuum-dried for 10 min, and the residue was co-evaporated with dry toluene twice and then vacuum-dried at 60° C. to obtain 53.99 g of a white crystalline solid.

S12: at a temperature of 0° C., 11.3 mL of n-butyl chloroformate (89 mmol, 1.5 equiv) was added into 296 mL of a dichloromethane solution containing 28.05 g of the aforementioned white crystalline solid prepared by S11 (59 mmol) and 8.02 mL of N-methylimidazole (101 mmol, 1.7 equiv) to obtain a reaction mixture, and no precipitation occurred at that time; the reaction mixture was stirred at room temperature (at 15-25° C., similarly hereinafter) for 4 h, then the solvent was removed through evaporation at 30° C. to obtain a residue; 197 mL of methanol and 41 mL of triethylamine (0.27 mol, 5 equiv) were added into the residue to obtain a mixture, and the mixture was stirred at room temperature overnight, and thin-layer chromatography, i.e., TLC, performed on the next day showed that almost all of the mixture were product.

The solvent was removed from the mixture through evaporation, and the residue was dissolved in 500 mL of a mixed solution of ethyl acetate/dichloromethane (1:3), and then mixed and shaken together with 300 mL of a citric acid solution (containing 42 g of citric acid) in a separating funnel. The organic layer was directly poured into a filter funnel containing 100 g of silica gel, and the aqueous phase was extracted for 3 times with 200 mL of the mixed solvent of ethyl acetate/dichloromethane (1:3), and then sequentially eluted with 100 mL of the mixed solvent of ethyl acetate/dichloromethane (1:3) and 300 mL of a mixed solvent of methanol/dichloromethane (1:20) to obtain a product, and the product was eluted with 1300 mL of the mixed solvent of methanol/dichloromethane (1:20). After removal of the solvent through evaporation and vacuum-dried at 60° C., obtain 19.8 g of a white solid foam intermediate G1 was obtained with a yield of 92.0% (counted by gemcitabine).

FIG. 1 shows the $^1$H-NMR spectrogram of the intermediate G1.

$^1$H NMR (399.86 MHz, DMSO-$d_6$): δ=0.90 (t, 3H, $^3J$=7.42 Hz, CH$_3$), 1.30-1.41 (m, 2H, CH$_2$CH$_2$CH$_2$CH$_3$), 1.54-1.64 (m, 2H, CH$_2$CH$_2$CH$_2$CH$_3$), 3.65 (dm, 1H, $^2J$=12.69 Hz, $^3J$=3.22 Hz, H-5a'), 3.81 (dm, 1H, $^2J$=12.69 Hz, H-5b'), 3.86-3.91 (m, 1H, H-4'), 4.12 (t, 2H, $^3J$=6.64 Hz, CH$_2$CH$_2$CH$_2$CH$_3$), 4.13-4.25 (m, 1H, H-3'), 5.30 (t, 1H, $^3J$=5.37 Hz, OH-5'), 6.17 (t, 1H, $^3J_{(H-F)}$=7.52 Hz, H-1'), 6.32 (d, 1H, $^3J$=6.45 Hz, OH-3'), 7.10 (d, 1H, $^3J$=7.71 Hz, H-5), 8.22 (d, 1H, $^3J$=7.71 Hz, H-6), 10.84 (br s, 1H, NH).

LC/MS(ESI)[M+H]$^+$ theoretical value: 364.13, and measured value: 364.17.

S2: the intermediate G2 was prepared, with a synthesis route as follows:

-continued

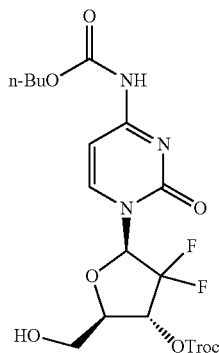

The specific method is as follows:

1.5 g of the intermediate G1 (4.1 mmol) prepared by step S1, 0.653 g of tert-butyldimethylchlorosilane (4.3 mmol, 1.05 equiv) and 0.765 mL of pyridine (9.5 mmol, 2.3 equiv) were dissolved in 15 mL of dichloromethane and stirred at room temperature for 1 h, and TLC result indicated that half of the reaction was done. The reaction mixture was stirred overnight, and still a large quantity of intermediates G1 were present, then 0.187 g of tert-butyldimethylchlorosilane (1.24 mmol, 0.3 equiv) was added, the reaction mixture was stirred at room temperature for 6 h, and the TLC showed that there is still some of the intermediate G1 left. Then 0.124 g of tert-butyldimethylchlorosilane (0.83 mmol, 0.2 equiv) was added into the reaction mixture and continually stirred overnight, and the TLC of the next day showed that there was no intermediate G1, thereafter 0.2-33 mL of pyridine (2.9 mmol, 0.7 equiv) was added and then 0.625 mL of 2,2,2-trichloro-ethyl chloroformate (4.5 mmol, 1.1 equiv) was added at 0° C., and the reaction mixture was stirred at room temperature for 0.5 h, and the TLC showed that the reaction was completed.

The reaction mixture was shaken together with 3.90 g of citric acid (18.6 mmol, 4.5 equiv). The extract obtained after the solvent was removed through evaporation did not need to be dried, and the residue was dried under high vacuum at 40° C. and then dissolved in 27 mL of tetrahydrofuran. The solution was cooled to 0° C., and added with triethylamine and 3 times of hydrofluoric acid. The solution was placed in a refrigerator at 5° C. overnight, and in the next day the reaction mixture was maintained at 20° C. for 3 h, and then the solvent was removed through evaporation at this temperature. The residue was subjected to silica gel column chromatography (containing 55 g of silica gel), and then sequentially eluted with 500 mL of a mixed solvent of ethyl acetate/dichloromethane (1:5) and 450 mL of a mixed solvent of ethyl acetate/dichloromethane (1:2). The same constituents were combined, and then vacuum-dried at 60° C. after the solvent was removed through evaporation, so as to obtain 1.904 g of a white solid foam intermediate G2 with a yield of 86%.

Figure 2:
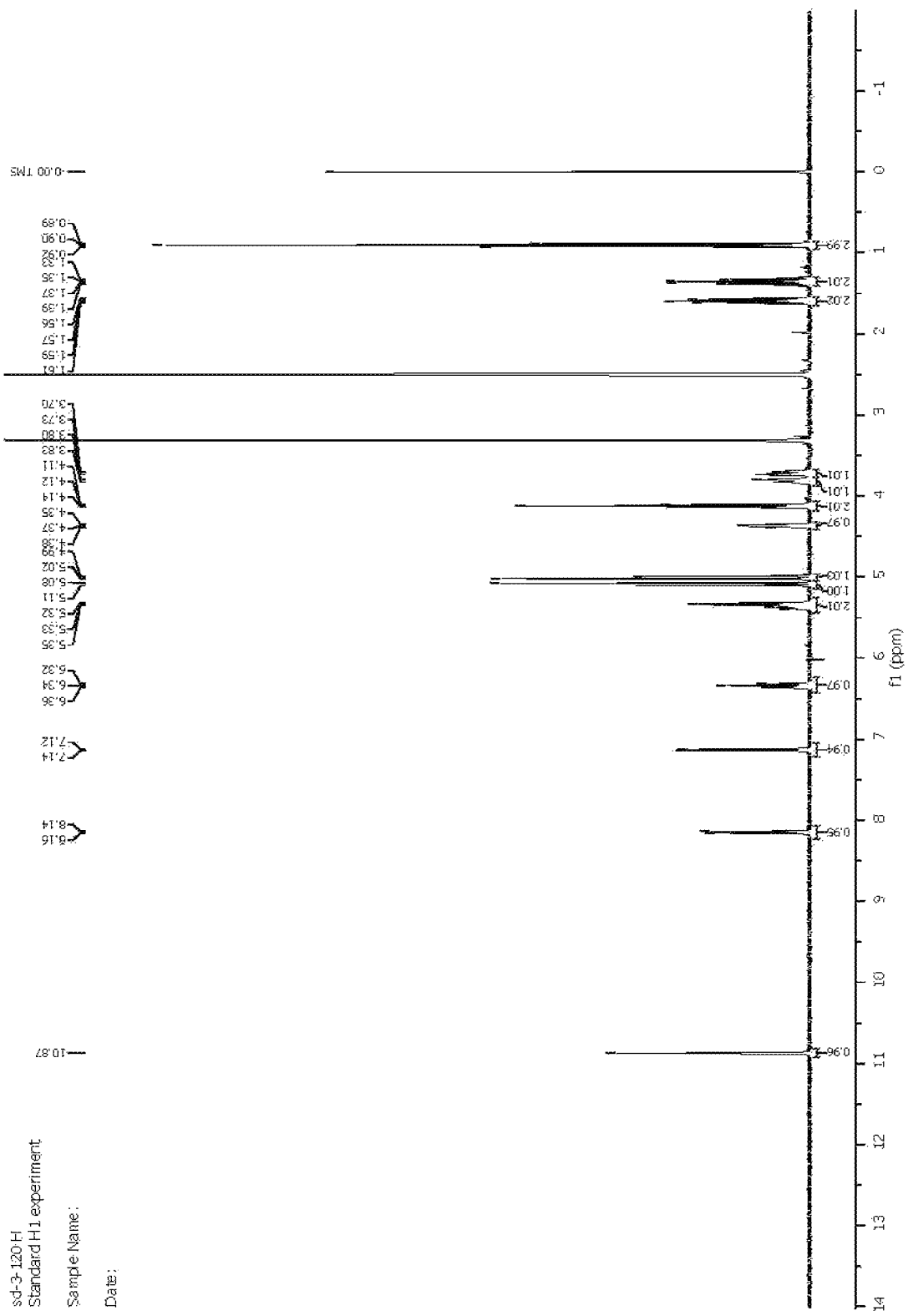
FIG. 2 is a $^1$H-NMR spectrogram of the intermediate G2.

FIG. 2 shows the $^1$H-NMR spectrogram of the intermediate G2.

$^1$H NMR (399.86 MHz, DMSO-$d_6$): δ=0.90 (t, 3H, $^3$J=7.32 Hz, CH$_2$CH$_2$CH$_2$CH$_3$), 1.30-1.41 (m, 2H, CH$_2$CH$_2$CH$_2$CH$_3$), 1.55-1.64 (m, 2H, CH$_2$CH$_2$CH$_2$CH$_3$), 3.68-3.76 (m, 1H, H-5a'), 3.78-3.85 (m, 1H, H-5b'), 4.12 (t, 2H, $^3$J=6.64 Hz, CH$_2$CH$_2$CH$_2$CH$_3$), 4.34-4.39 (m, 1H, H-4'), 5.01 (d, 1H, $^2$J=12.20 Hz, Troc), 5.09 (d, 1H, $^2$J=12.20 Hz, Troc), 5.31-5.41 (m, 2H, H-3', OH-5'), 6.34 (t, 1H, $^3$J$_{(H-F)}$=8.60 Hz, H-1'), 7.13 (d, 1H, $^3$J=7.62 Hz, H-5), 8.15 (d, 1H, $^3$J=7.62 Hz, H-6), 10.87 (br s, 1H, NH).

LC/MS(ESI)[M+H]$^+$ theoretical value: 538.0, and measured value: 538.2.

S3: the intermediate D1 was prepared, with a synthesis route as follows:

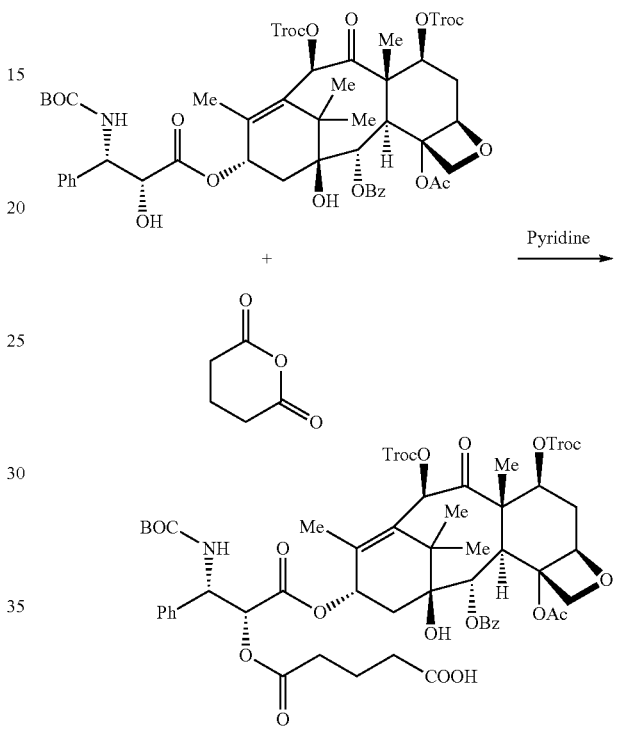

The specific method is as follows:

0.95 g of 7,10-di-troc-docetaxel (0.82 mmol) and 0.935 g of glutaric anhydride (8.2 mmol, 10 equiv) were dissolved in 10.6 mL of pyridine (131 mmol, 160 equiv), and the reaction mixture was stirred at room temperature for 2.5 h and then placed in a refrigerator at −20° C. overnight; in the next day the reaction mixture was stirred at room temperature for more than 3 h, and the TLC showed that the reaction was substantially completed.

The pyridine was removed through evaporation at 30° C., and the residue was vacuum-dried at this temperature and then dissolved in a solution of 5.5 g citric acid (26 mmol, 32 equiv) and then extracted with dichloromethane. The extract was poured directly into a silica gel column (containing 20 g of silica gel), the impurities were washed away with 110 mL of the mixed solvent of methanol/dichloromethane (1:100), and the product was eluted with 143 mL of the mixed solvent of methanol/dichloromethane (1:100) and 102 mL of a mixed solvent of methanol/dichloromethane (1:50), and then vacuum-dried at 40° C. after the solvent was removed through evaporation; as a result, 1.055 g of a white solid crude product of the intermediate D1 was obtained.

The crude product was subjected to silica gel column chromatography (containing 35 g of silica gel), and then sequentially eluted with 50 ml of dichloromethane, 210 mL of a mixed solvent of ethyl acetate/dichloromethane (1:20) and 220 mL of a mixed solvent of ethyl acetate/dichloromethane (1:10) to wash impurities away, and the eluted constituents were collected into a test tube and subjected to column elution with a mixed solvent of ethyl acetate/dichloromethane (1:5). The same constituents were combined, and then vacuum-dried at 40° C. after the solvent was removed through evaporation, so as to obtain 0.623 g of a white solid finished product of the intermediate D1 with a yield of 60%.

Figure 3:
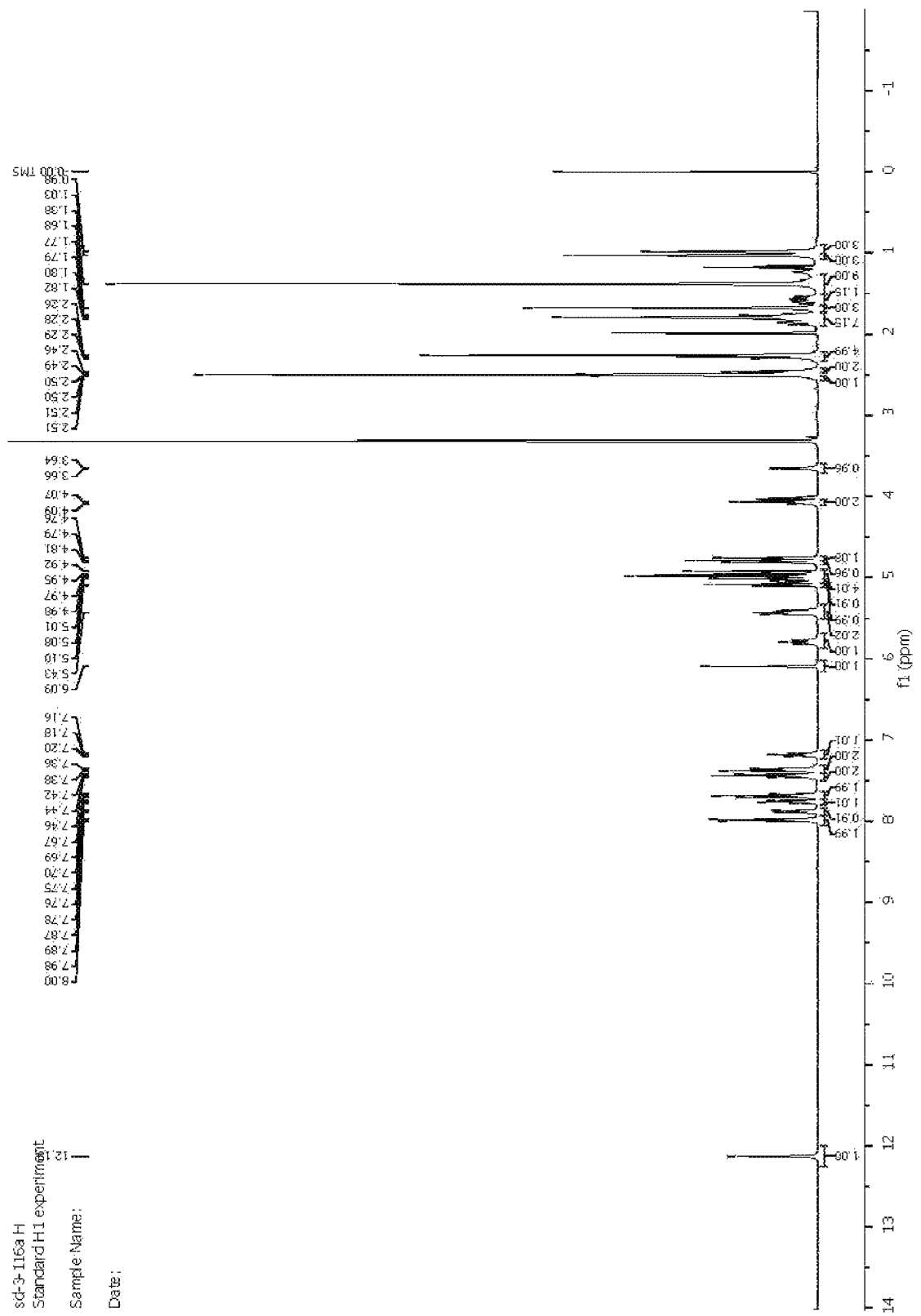
FIG. 3 is a $^1$H-NMR spectrogram of the intermediate D1.

FIG. 3 shows the $^1$H-NMR spectrogram of the intermediate D1.

$^1$H NMR (399.86 MHz, DMSO-d$_6$): δ=0.98 (s, 3H, CH$_3$), 1.03 (s, 3H, CH$_3$), 1.38 (s, 9H, BOC), 1.51-1.65 (m, 1H), 1.68 (s, 3H, CH$_3$), 1.72-1.91 (m, 4H), 1.80 (s, 3H, CH$_3$), 2.26 (s, 3H, OAc), 2.28 (t, 2H, $^3$J=7.42 Hz, COCH$_2$CH$_2$CH$_2$COOH), 2.46 (t, 2H, $^3$J=7.23 Hz, COCH$_2$CH$_2$CH$_2$COOH), 2.56-2.50 (m, 1H), 3.65 (d, 1H, $^3$J=6.83 Hz, CH), 4.03-4.10 (m, 2H), 4.77 (d, 1H, $^2$J=12.01 Hz, Troc-a), 4.81 (s, 1H), 4.93 (d, 1H, $^2$J=12.01 Hz, Troc-a), 4.95 (d, 1H, $^2$J=12.10 Hz, Troc-b), 4.98-5.02 (m, 1H), 5.00 (d, 1H, $^2$J=12.10 Hz, Troc-b), 5.01-5.07 (m, 1H), 5.09 (d, 1H, $^3$J=8.40 Hz), 5.38-5.47 (m, 2H), 5.79 (t, 1H, $^3$J=8.89 Hz, CH), 6.09 (s, 1H), 7.18 (t, 1H, $^3$J=7.32 Hz, CH$_{p\text{-}Ph}$), 7.37 (d, 2H, $^3$J=7.62 Hz, CH$_{o\text{-}Ph}$), 7.41-7.47 (m, 2H, CH$_{m\text{-}Ph}$), 7.65-7.72 (m, 2H, CH$_{m\text{-}Bz}$), 7.76 (t, 1H, $^3$J=7.32 Hz, CH$_{p\text{-}Bz}$), 7.88 (d, 1H, $^3$J=8.98 Hz, NH—BOC), 7.99 (d, 2H, $^3$J=7.22 Hz, CH$_{o\text{-}Bz}$), 12.13 (br s, 1H, COOH).

LC/MS(ESI)[M+Na]$^+$ theoretical value: 1292.2, and measured value: 1292.2.

S4: the intermediate D2 was prepared, with a synthesis route as follows:

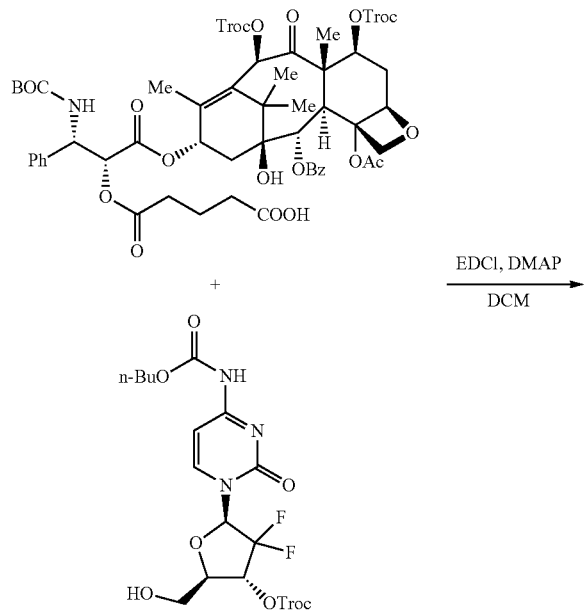

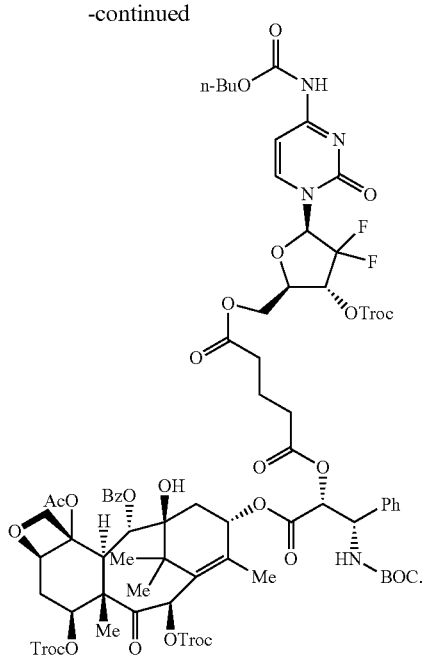

The specific method is as follows:

At a temperature of 0° C., 0.277 mg of the intermediate G2 (0.51 mmol, 1.1 equiv) prepared by the step S2, 0.594 mg of the intermediate D1 (0.47 mmol, 1 equiv) prepared by the step S3, 98 mg of carbodiimide (0.51 mmol, 1.1 equiv) and 11.4 mg of 4-dimethylaminopyridine (95·10$^{-6}$ mol, 0.2 equiv) were dissolved into 0.934 mL of dichloromethane, and the reaction mixture was slowly warmed to room temperature and stirred overnight, and the TLC of the next day showed that there were main products and some minor impurities.

The reaction mixture was poured directly into a silica gel column (containing 35 g of silica gel), and then sequentially eluted with 50 mL of dichloromethane, 205 mL of a mixed solvent of ethyl acetate/dichloromethane (1:40), 210 mL of a mixed solvent of ethyl acetate/dichloromethane (1:20) and 220 mL of a mixed solvent of ethyl acetate/dichloromethane (1:10) to wash impurities away. The eluted constituents were collected into a test tube and subjected to column elution with 360 mL of a mixed solvent of ethyl acetate/dichloromethane (1:5). The same constituents were combined, and then vacuum-dried at 40° C. after the solvent was removed through evaporation, so as to obtain 0.636 g of colorless transparent intermediate D2 with a yield of 76%.

Figure 4:
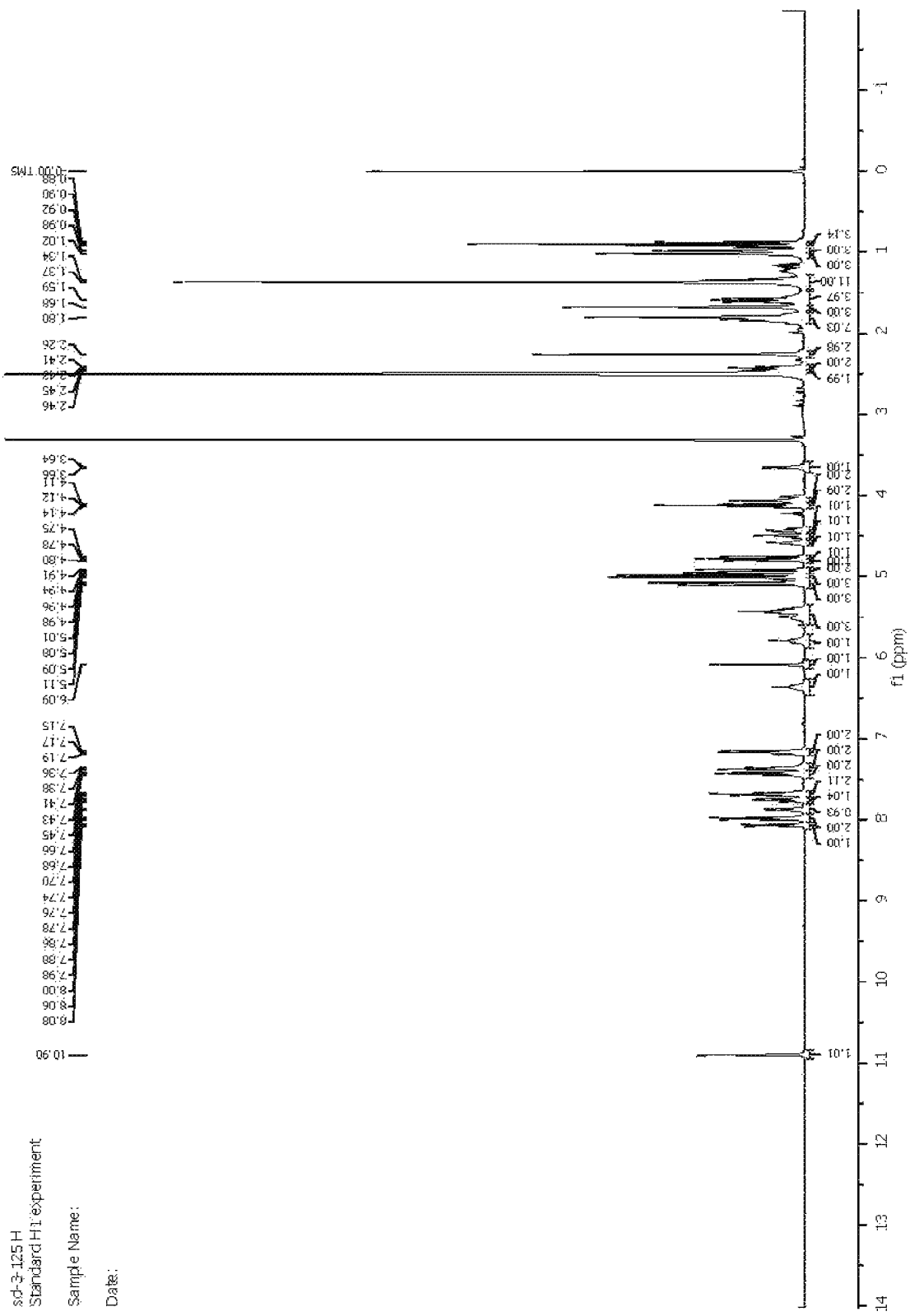
FIG. 4 is a $^1$H-NMR spectrogram of the intermediate D2.

FIG. 4 shows the $^1$H-NMR spectrogram of the intermediate D2.

$^1$H NMR (399.86 MHz, DMSO-d$_6$): δ=$^1$H NMR (399.86 MHz, DMSO-d$_6$): δ=0.90 (t, 3H, $^3$J=7.32 Hz, CH$_2$CH$_2$CH$_2$CH$_3$), 0.98 (s, 3H, CH$_3$), 1.02 (s, 3H, CH$_3$), 1.30-1.41 (m, 2H, CH$_2$CH$_2$CH$_2$CH$_3$), 1.37 (s, 9H, BOC), 1.51-1.66 (m, 4H, CH$_2$CH$_2$CH$_2$CH$_3$, CH$_2$-a, CH$_2$-a), 1.68 (s, 3H, CH$_3$), 1.75-1.89 (m, 4H), 1.80 (s, 3H, CH$_3$), 2.26 (s, 3H, OAc), 2.43 (t, 2H, $^3$J=7.52 Hz, COCH$_2$CH$_2$CH$_2$CO), 2.46 (t, 2H, $^3$J=8.01 Hz, COCH$_2$CH$_2$CH$_2$CO), 3.65 (d, 1H, $^3$J=6.64 Hz, CH), 4.03-4.10 (m, 2H), 4.12 (t, 2H, $^3$J=6.64 Hz, CH$_2$CH$_2$CH$_2$CH$_3$), 4.43 (dd, 1H, $^2$J=12.10 Hz, $^3$J=6.25 Hz, H-5'a), 4.51 (dd, 1H, $^2$J=12.10 Hz, $^3$J=2.84 Hz, H-5'b), 4.55-4.62 (m, 1H, H-4'), 4.77 (d, 1H, $^2$J=12.11 Hz, Troc-a), 4.80 (s, 1H), 4.93 (d, 1H, $^2$J=12.11 Hz, Troc-a), 4.94 (d, 1H, $^2$J=12.10 Hz, Troc-b), 4.97-5.20 (m, 3H), 5.01-5.10 (m, 2H), 5.09 (d, 1H, $^2J$=12.30 Hz, Troc-c), 5.37-5-57 (m, 3H), 5.80 (t, 1H, $^3J$=8.98 Hz, CH), 6.09 (s, 1H), 6.36 (t, 2H, $^3J_{(H\text{-}F)}$=8.30 Hz, H-1'), 7.16 (d, 1H, $^3J$=7.61 Hz, H-5), 7.18 (t, 1H, $^3J$=7.42 Hz, $CH_{p\text{-}Ph}$), 7.37 (d, 2H, $^3J$=7.62 Hz, $CH_{o\text{-}Ph}$), 7.40-7.47 (m, 2H, $CH_{m\text{-}Ph}$), 7.65-7.72 (m, 2H, $CH_{m\text{-}Bz}$), 7.76 (t, 1H, $^3J$=7.42 Hz, $CH_{p\text{-}Bz}$), 7.87 (d, 1H, $^3J$=8.98 Hz, NH—BOC), 7.99 (d, 2H, $^3J$=7.42 Hz, $CH_{o\text{-}Bz}$), 8.07 (d, 1H, $^3J$=7.42 Hz, H-6), 10.90 (br s, 1H, NH).

LC/MS(ESI)[M+H−Troc]$^+$ theoretical value: 1617.3, and measured value: 1617.6.

S5: the new type of taxane Z1 was prepared, with a synthetic route as follows:

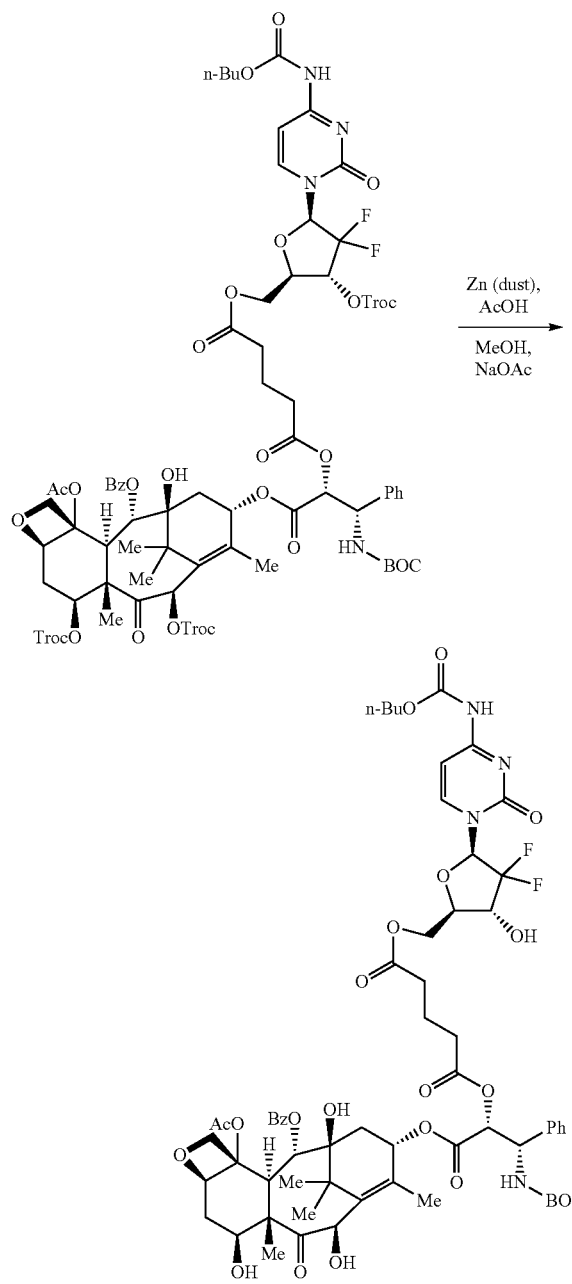

The specific method is as follows:

1.101 g of sodium acetate (13.4 mmol, 40 equiv) was dissolved in a mixed solution of 12 mL methanol and 12 mL acetic acid, and the solution was then added into a flask filled with 0.602 g of the intermediate D2 (0.34 mmol) prepared by the step S4, and when the intermediate was completely dissolved, 1.756 g of zinc powder (27 mmol, 40 equiv) was added, the reaction mixture was subjected to ultrasonic vibration at 5° C. for 15 min and shaken vigorously, and the TLC showed that the intermediate D2 was disappeared, and there was only a trace amount of the di(trichloroethoxycarbonyl) product and a certain amount of mono(trichloroethoxycarbonyl) product, and the vast majority of the product was the target product. The ultrasonic vibration was continued and the vigorous shaken was sustained for 15 min. TLC showed that there was no di(trichloroethoxycarbonyl) product, but there was still some mono(trichloroethoxycarbonyl). The reaction mixture was subjected to ultrasonic vibration for the third time and shaken vigorously for 15 min, then poured into 50 mL of an aqueous suspension containing 19.44 g sodium bicarbonate (0.23 mol), then added with ethyl acetate and filtered, the filtrate was extracted with ethyl acetate, and the extract was evaporated to dryness at 25° C.

The residue was dissolved in dichloromethane and then subjected to silica gel column chromatography (35 g of silica gel), and then sequentially eluted with 203.3 mL of a mixed solvent of methanol/dichloromethane (1:60) and 615 mL of a mixed solvent of methanol/dichloromethane (1:40). The eluted constituents were collected into a test tube, and then sequentially eluted with 206.7 mL of a mixed solvent of methanol/dichloromethane (1:30) and 208 mL of a mixed solvent of methanol/dichloromethane (1:25). The same constituents were combined, and then vacuum-dried at 40° C. after the solvent was removed through evaporation, so as to obtain 0.244 g of a colorless transparent target product Z1, with a yield of 57% and purity of 95.0% (HPLC).

Figure 5:
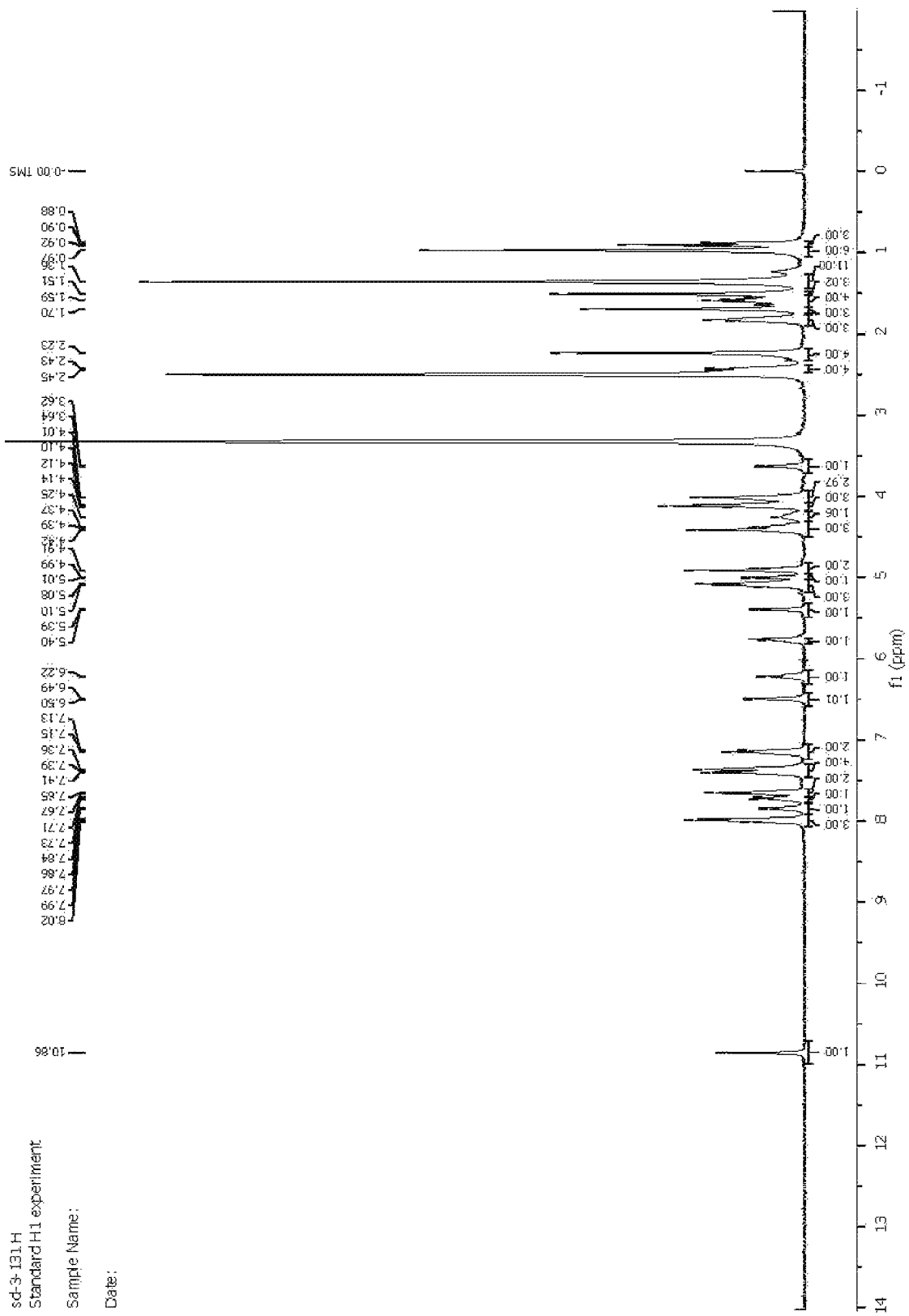
FIG. 5 is a $^1$H-NMR spectrogram of a new type of taxane compound Z1.
Figure 6:
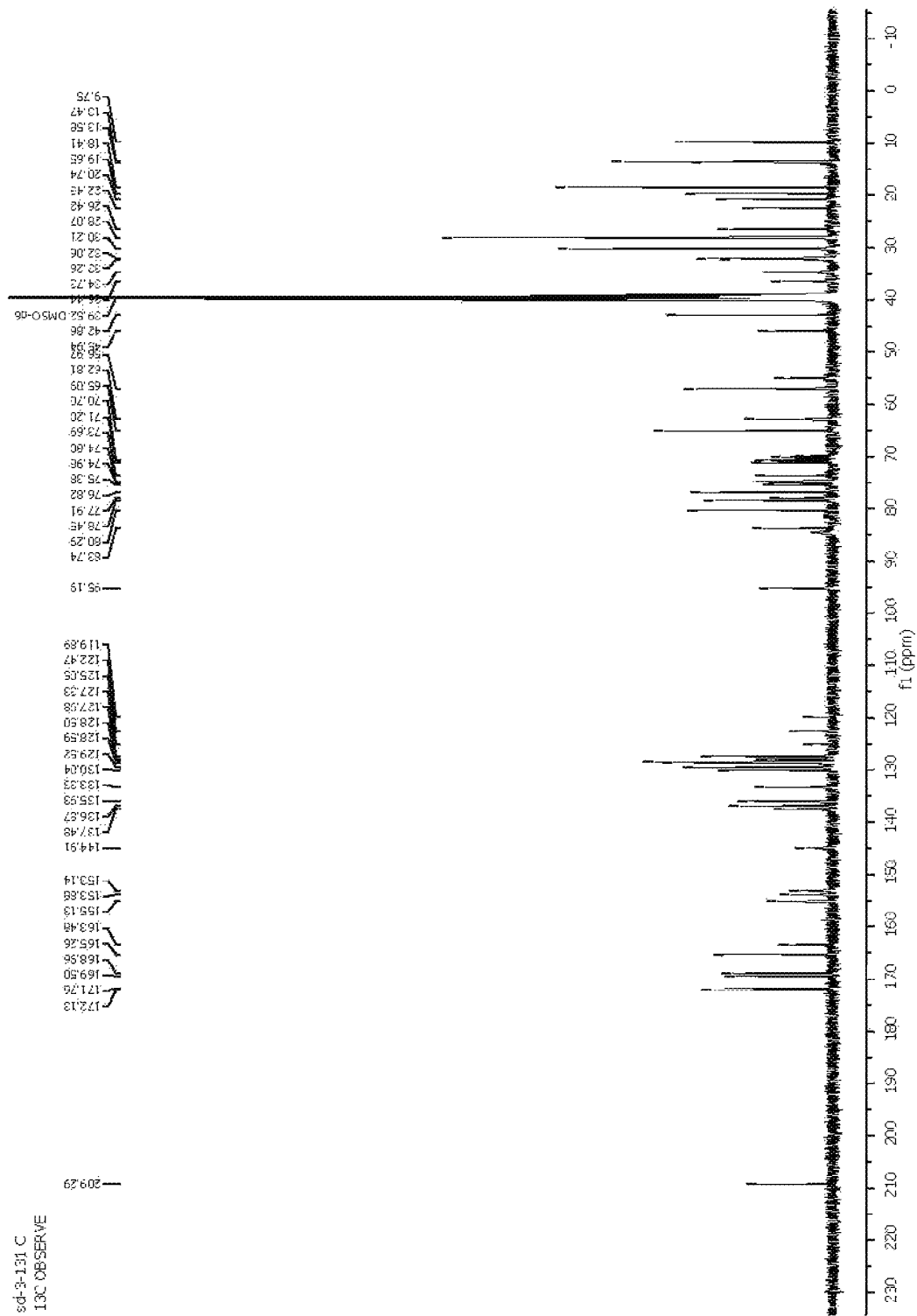
FIG. 6 is a $^{13}$C-NMR spectrogram of the new type of taxane compound Z1.
Figure 7:
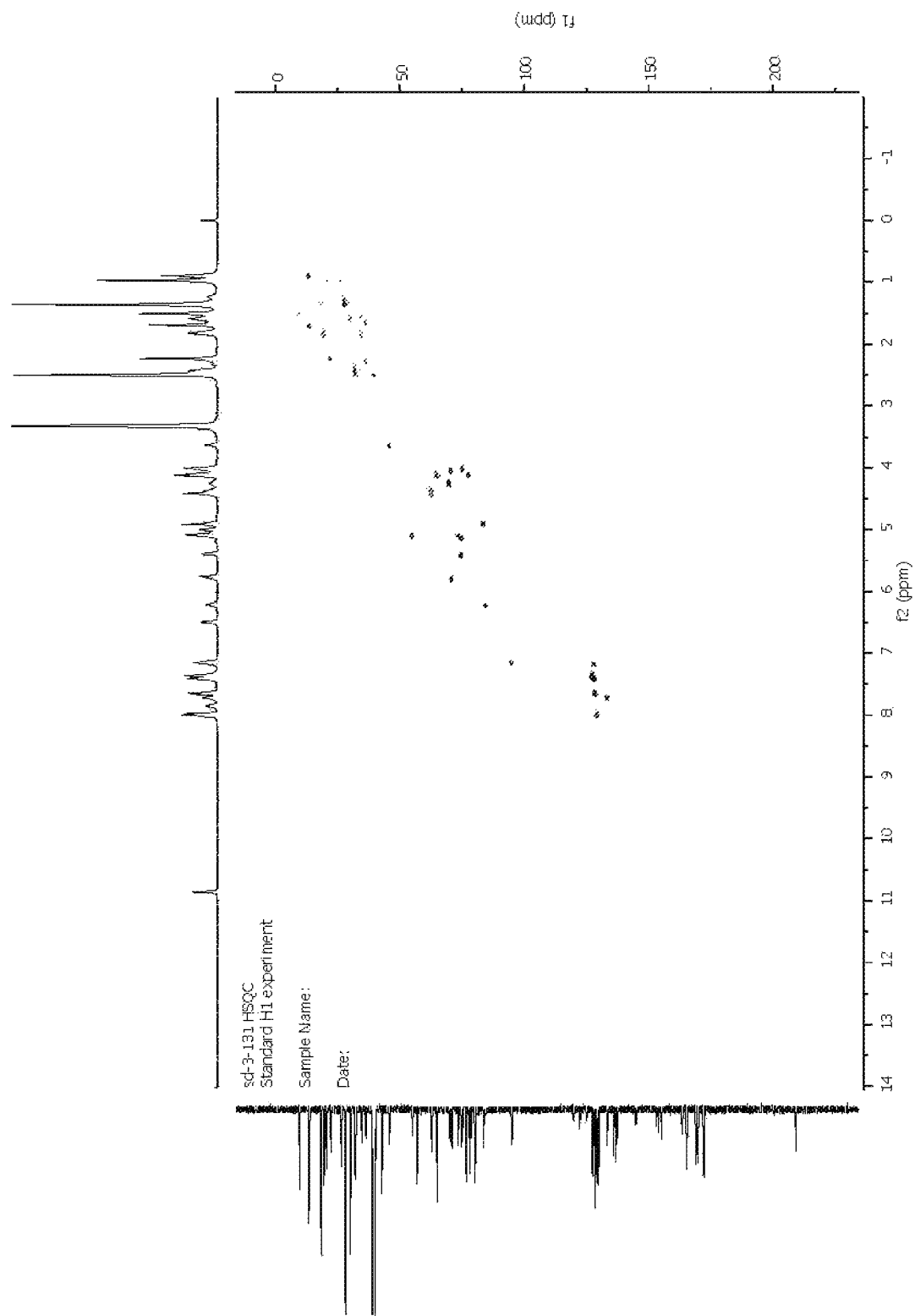
FIG. 7 is a HSQC diagram (heteronuclear single quantum correlation spectrogram) of the new type of taxane compound Z1.

FIGS. 5-7 respectively shows the $^1$H-NMR spectrogram, $^{13}$C-NMR spectrogram and HSQC spectrogram of the target product Z1.

$^1$H NMR (399.86 MHz, DMSO-$d_6$): δ=0.90 (t, 3H, $^3J$=7.13 Hz, $CH_2CH_2CH_2CH_3$), 0.97 (s, 6H, $CH_3$×2), 1.29-1.41 (m, 2H, $CH_2CH_2CH_2CH_3$), 1.36 (s, 9H, BOC), 1.51 (s, 3H, $CH_3$), 1.53-1.67 (m, 4H, $CH_2CH_2CH_2CH_3$, $CH_2$-a, $CH_2$-a), 1.70 (s, 3H, $CH_3$), 1.76-1.89 (m, 3H, $COCH_2CH_2CH_2CO$, $CH_2$-b), 2.23 (s, 3H, OAc), 2.25-2.33 (m, 1H, $CH_2$-b), 2.38-2.48 (m, 4H, $COCH_2CH_2CH_2CO$), 3.63 (d, 1H, $^3J$=6.44 Hz, CH), 3.97-4.07 (m, 3H, CH, $CH_2O$), 4.06-4.12 (m, 1H, H-4'), 4.12 (t, 2H, $^3J$=6.44 Hz, $CH_2CH_2CH_2CH_3$), 4.18-4.31 (m, 1H, H-3'), 4.32-4.47 (m, 3H, H-5', t-OH), 4.86-4.95 (m, 2H, CH, OH), 5.00 (d, 1H, $^3J$=6.64 Hz, OH), 5.03-5.14 (m, 3H, CH×3), 5.40 (d, 1H, $^3J$=6.83 Hz, CH), 5.77 (t, 1H, $^3J$=8.59 Hz, CH), 6.22 (t, 2H, $^3J_{(H\text{-}F)}$=7.52 Hz, H-1'), 6.49 (d, 1H, $^3J$=6.06 Hz, OH-3'), 7.10-7.20 (m, 2H, H-5, $H_{p\text{-}Ph}$), 7.31-7.45 (m, 4H, $H_{o\text{-}Ph}$×2, $H_{m\text{-}Ph}$×2), 7.61-7.69 (m, 2H, $H_{m\text{-}Ph}$), 7.73 (t, 1H, $^3J$=7.42 Hz, $H_{p\text{-}Ph}$), 7.85 (d, 1H, $^3J$=8.98 Hz, NH—BOC), 7.93-8.04 (m, 3H, $H_{o\text{-}Ph}$×2, H-6), 10.86 (br s, 1H, NH).

$^{13}$C NMR (100.56 MHz, DMSO-$d_6$): δ=9.8 ($CH_3$), 13.5 ($CH_2CH_2CH_2CH_3$), 13.6 ($CH_3$), 18.4 ($CH_2CH_2CH_2CH_3$), 19.7 ($COCH_2CH_2CH_2CO$), 20.7 ($CH_3$), 22.4 (OAc), 26.4 ($CH_3$), 28.1 (t-BOC, primary), 30.2 ($CH_2CH_2CH_2CH_3$), 32.1 ($COCH_2CH_2CH_2CO$), 32.3 ($COCH_2CH_2CH_2CO$), 34.7 ($CH_2$), 36.4 ($CH_2$), 42.9, 45.9 (CH), 55.1 (CH), 57.0, 62.8 ($CH_2$-5'), 65.1 ($CH_2CH_2CH_2CH_3$), 70.1 (t, $^2J_{(C\text{-}F)}$=23.0

Hz, CH-3'), 70.7 (CH), 71.2 (CH), 73.7 (CH), 74.8 (CH), 75.0 (CH), 75.4 (CH$_2$), 76.8, 77.9 (CH-4'), 78.5, 80.3 (t-BOC, quaternary), 83.7 (CH), 84.5 (br s, CH-1'), 95.2 (CH-5), 122.5 (t, $^1J_{(C-F)}$=259.2 Hz, C-2'), 127.3 (CH$_{o-Ph}$), 128.0 (CH$_{p-Ph}$), 128.5 (CH$_{m-Ph}$), 128.6 (CH$_{m-Ph}$), 129.5 (CH$_{o-Ph}$), 130.0, 133.3 (CH$_{p-Ph}$), 135.9, 136.9, 137.5, 144.9 (CH-6), 153.1 (NHCOO), 153.9 (CO$_{Ar}$), 155.1 (NHCOO), 163.5 (C-4), 165.3 (COO), 169.0 (COO), 169.5 (COO), 171.8 (COCH$_2$CH$_2$CO), 172.1 (COCH$_2$CH$_2$CO), 209.3 (CO).

LC/MS(ESI)[M+H]$^+$ theoretical value: 1267.5, and measured value: 1267.8.

Example 2-Example 9

The preparation method of each example is substantially the same as that of Example 1, except the type of alkyl chloroformate used in the step S1 and the type of dianhydride used in the step S3; where the finally obtained new type of taxane compounds were shown in Table 1.

TABLE 1

| No. of Example | No. of Compound | Alkyl Chloroformate | Dianhydride | R$^1$ | n |
|---|---|---|---|---|---|
| Example 1 | Z1 | n-butyl Chloroformate | Glutaric Anhydride | n-butyl | 1 |
| Example 2 | Z2 | n-butyl Chloroformate | Adipic Anhydride | n-butyl | 2 |
| Example 3 | Z3 | n-butyl Chloroformate | Succinic Anhydride | n-butyl | 0 |
| Example 4 | Z4 | n-hexyl Chloroformate | Glutaric Anhydride | n-hexyl | 1 |
| Example 5 | Z5 | n-hexyl Chloroformate | Adipic Anhydride | n-hexyl | 2 |
| Example 6 | Z6 | n-hexyl Chloroformate | Succinic Anhydride | n-hexyl | 0 |
| Example 7 | Z7 | Ethyl Chloroformate | Glutaric Anhydride | Ethyl | 1 |
| Example 8 | Z8 | Ethyl Chloroformate | Adipic Anhydride | Ethyl | 2 |
| Example 9 | Z9 | Ethyl Chloroformate | Succinic Anhydride | Ethyl | 0 |

Example 10

This Example is a method for producing a pharmaceutical composition containing the new type of taxane compound Z1 of Example 1.

Taking freeze-dried powder injection as an example of the injection dosage form, the freeze-dried powder injection included: 30 g of the new type of taxane compound Z1, 300 g of mannitol (20%, w/v), 7 g of a buffer of sodium dihydrogen phosphate dihydrate, and 4.0 g of a surfactant of poloxamer 188 (F68).

Sodium dihydrogen phosphate dihydrate, poloxamer 188 (F68), mannitol (20%, w/v) were accurately weighed according to the above prescription amount, and then added into and dissolved in 300 g of water for injection which was pre-cooled to below 10° C., and the pH of the solution was adjusted to 7.3-7.5 with 0.1 mol/L of NaOH; then 30 g of the new type of taxane compound Z1 was added into the aforementioned solution and mixed uniformly, and the pH of the solution was adjusted to 7.3±0.2 (7.5 in this example) with 0.1 mol/L of a NaOH solution or 0.1 mol/L of HCl; water was added to 2,000 g, and the solution was filtered through a 0.22 μm microporous membrane for sterilization; and the solution was distributed into tube-type bottles according to 2.0 g per bottle, partially stoppered and placed in a freeze dryer for freeze-drying, vacuum-plugged after the drying, capped and labeled to obtain 1,000 freeze-dried powder injections and store the same at a temperature of 2-8° C.

In addition to the aforementioned freeze-dried powder injection, i.e., a sterile powder for injection, the new type of taxane compound of the present disclosure can also be prepared into other forms of injection dosage forms, such as a solution injection, a suspension injection, and an emulsion injection.

In addition to the tablet form described above, suitable dosage forms of the pharmaceutical composition may also be formulated into oral powders, granules, capsules, pellets, solutions, suspensions, emulsions, syrups or elixirs, or a sustained-release and controlled-release preparation in an oral form, or pharmaceutical compositions of other oral forms. These oral dosage forms contained common corresponding adjuvant materials (divided into additives, adjuvants, and the like according to different effects), where for example the additives included mannitol, lactose, starch, magnesium stearate, saccharin salt, cellulose or magnesium sulfate and the like of drug grades.

In achieving of the aforementioned oral dosage forms, a pharmaceutically acceptable adjuvant might be selected as a carrier for the pharmaceutically active components, including a substance with matured prior art, such as an inert solid diluent, an aqueous solvent, a liposome, a microsphere and/or a non-toxic organic solvent, etc.; preferred adjuvants are: humidizers, emulsifiers, pH buffering solutions, human serum albumin, antioxidants, preservatives, bacteriostats, glucose, sucrose, trehalose, maltose, lecithin, glycine, sorbic acid, propylene alcohol, polyethylene, protamine, boric acid, sodium chloride, or potassium chloride, mineral oil, vegetable oil, etc.; one or more combinations may be selected from them as a pharmaceutical carrier.

The target tumor of the pharmaceutical composition of the present disclosure includes a blood tumor or a malignant solid tumor. Specifically, the target tumor includes a colon cancer, a rectal cancer, a gastric cancer, a lung cancer, a breast cancer, a prostate cancer, a pancreatic cancer, a liver cancer, an esophageal cancer, a brain tumor, an ovarian cancer, an uterine cancer, a kidney cancer, a head and neck cancer, a skin cancer, a bladder cancer, a vulvar cancer, a testicular tumor, a villus cancer, a germ cell tumor, a malignant lymphoma, a leukemia and a multiple myeloma; and more preferably the target tumor could include a colon cancer, a rectal cancer, a gastric cancer, a lung cancer, a pancreatic cancer, a liver cancer, an ovarian cancer, a kidney cancer, a malignant lymphoma, a breast cancer and a leukemia, but the present disclosure was not limited thereto.

Application Example 1. Single Intraperitoneal Administration of the Disclosed Taxane Compound for a Maximal Tolerance Dose Experiment in ICR, i.e., Institute of Cancer Research, Mice This application example was to study the toxic response of ICR mice to the single intraperitoneal administration of the taxane compound Z1 of Example 1, so as to determine the maximum tolerance dose (MTD) of the disclosed taxane compound.

The maximum tolerance dose referred to a dose at which the animal did not die, the body weight of the animal did not exceed 10% (compared with that in Day 0), or no significant toxic side effect occurred.

1. Preparation of Substances to be Tested.

The sources of solvents used for dissolution of the substances to be tested are as follows:

Anhydrous ethanol, with a batch number of 10009218, manufacturer: Sinopharm Chemical Reagent Co. Ltd.

Cremophor EL, with a batch number of 27963, manufacturer: Sigma.

0.9% normal saline, with a batch number of 13083004, manufacturer: Hua Yu Pharmaceutical Co., Ltd.

A certain amount of a corresponding substance to be tested was weighed into a 5 mL glass test tube, and dissolved in ethanol under stirring by a 5 mm magnetic stir bar, and Cremophor EL was added after completely dissolving of the substance to be tested, stirring was maintained, and the labeled amount of normal saline was added and well stirred before use, where during formulation, the volume ratio of ethanol, Cremophor EL, and normal saline was 5:5:90.

2. Experimental Animal.

Varieties and strains: ICR mice.

Grade: SPF.

Gender: Female.

Source: Shanghai Slac Laboratory Animal Co. Ltd.

Certificate number: 0130749.

Body weight of the animal before the start of the experiment: 18-20 g.

Number and Gender: 41.

Time for adaption to environment: 5-7 days, under the same feeding conditions as that of the experiment.

The animal room was maintained at a temperature of 18-26° C., a relative humidity of 30-70%, and illumination for 12 h.

The water used for experimental animals was filtered and sterilized, and the animals were given ad libitum access to food and water.

3. Experimental Method.

Mode of administration: intraperitoneal injection (IP). If an animal died, the dose is reduced until the animals survived, and if there was no animal death, the dose was increased; if the animals were normally alive at a given high dose, the experiment was ended. Finally, the mouse MTD to the substance to be tested was determined according to the experimental results; and the animals were observed for continuous 7 days after acute administration.

For all animals during the experiment, all the animals to be tested were subjected to detailed clinical observation twice a day (one at 10:00 AM, and the other at 16:00 PM) after administration for continuous 14 days. The observation includes but not limited to: skin, hair, eyes, ears, nose, mouth, chest, abdomen, pudendum, limbs and feet, respiratory tract and circulatory system, autonomic effects (such as salivation), nervous systems (such as tremor, convulsions, stress responses, and abnormal behaviors).

The body weight of each animal was weighed before administration, and then the body weight of each animal was weighed and recorded at the same time in the following days.

Observation results, body weight of each animal, and animal survival conditions one week after the administration were recorded in detail on a daily basis.

4. Experimental Result.

The MTD dose of the disclosed taxane compound Z1 was 250 mg/kg.

Application Example 2. Growth Inhibition Effect of Single Intraperitoneal Injection of the Disclosed Taxane Compound on Tumor This application example is to study the growth inhibitory effect of single intraperitoneal injection of the disclosed taxane compound Z1 of Example 1 on colon cancer HCT-116 tumor-bearing nude mice.

1. Preparation of Substances to be Tested.

The sources of solvents used for dissolution of the substances to be tested are as follows:

Anhydrous ethanol, with a batch number of 10009218, manufacturer: Sinopharm Chemical Reagent Co., Ltd.

Cremophor EL, with a batch number of 27963, manufacturer: Sigma.

0.9% normal saline, with a batch number of 13083004, manufacturer: Hua Yu Pharmaceutical Co., Ltd.

A certain amount of a corresponding substance to be tested was weighed into a 5 mL glass test tube, and dissolved in ethanol under stirring by a 5 mm magnetic stir bar, and Cremophor EL was added after completely dissolving of the substance to be tested, stirring was maintained, and the labeled amount of normal saline was added and well stirred before use, where during formulation, the volume ratio of ethanol, Cremophor EL, and normal saline was 5:5:90.

2. Experimental Animal.

Varieties and strains: Balb/c Nude mice.

Grade: SPF.

Gender: Female.

Source: B&K Universal Group Limited, Shanghai.

Animal certificate number: 0123627.

Age of the animal at the start of the experiment: 7-9 weeks old.

Body weight of the animal at the start of the experiment: 18-22 g.

Time for adaption to environment: 5-7 days, under the same feeding conditions as that of the experiment.

The animal room environment was maintained at a temperature of 23±2° C., a humidity of 40-70%, and alternating light and dark for 12 h.

The animal feed (SLAC-M01) was purchased from Beijing Keao Xieli Feed Co., Ltd.

The water used for experimental animals was filtered and sterilized water, and the animals were given ad libitum access to food and water.

3. Experimental Method.

3.1. Tumor cells: colon cancer HCT-116 cells, purchased from Shanghai Institute of Biochemistry and Cell Biology (SIBCB), Chinese Academy of Sciences (CAS). The cells were cultured with a F-12 medium (containing 10% FBS) in a carbon dioxide incubator containing 5% by volume of $CO_2$ and 95% by volume of air, at 37° C. with saturated humidity. Before inoculation, cells at the logarithmic growth phase were taken, digested with 0.25% trypsin, washed once with PBS, and resuspended in PBS for counting. The cells were resuspended in a serum-free medium to adjust the cell concentration to about $3 \times 10^7$ cell/mL.

3.2. Animal inoculation and grouping: each nude mouse was subcutaneously inoculated with 0.1 mL of cell suspension ($3 \times 10^6$ cell/mouse) under sterile conditions. When the tumor grew to a volume of about 60-150 mm³, nude mice with similar tumor volumes and good shapes were selected (the shape is as single spherical as possible, without any irregular shape or gathered tumors), with 6 mice per group.

3.3. Animal Administration and Observation.

(1) the tumor formation conditions at the inoculation site of each nude mouse in each group were observed, the diameter of a tumor nodule (D) was measured with a round hole ruler for 3 times per week, and the volume (V) of the tumor nodule was calculated according to the following equation:

$$V = 3/4\pi (D/2)^3.$$

(2) The evaluation index of the anti-tumor activity was the tumor growth inhibition rate TGI (%), and the calculation equation thereof was:

$$TGI(\%) = (V_{control} - V_{Treatment})/V_{control} \times 100\%.$$

The body weight of each mouse was weighed 3 times a week.

3.4. Clinical Symptoms.

All clinical symptoms of each animal at the beginning of the experiment and during the experiment should be recorded. Observations should be made at the same time every day.

If the weight reduced by more than 20% or agony animal or tumor exceeded 2,800 mm³ in volume after the substance to be tested was administrated, then the animal was sacrificed by $CO_2$, the tumor was isolated and weighed, and the sacrificed animal was subjected to autopsy and visual observation to see if there was diseased organ.

3.5. Data Statistics.

The experimental data is expressed by Mean±SEM unless otherwise specified; and an unpaired T test is adopted on data of two groups, and it was considered that there is a significant difference if P<0.05.

4. Experimental Result.

The growth inhibition rate (TGI %) of the disclosed taxane compound Z1 against human colon cancer HCT-116 tumor-bearing mice was 85.69%.

What is claimed is:

1. A taxane compound, having a structure as shown in formula (I):

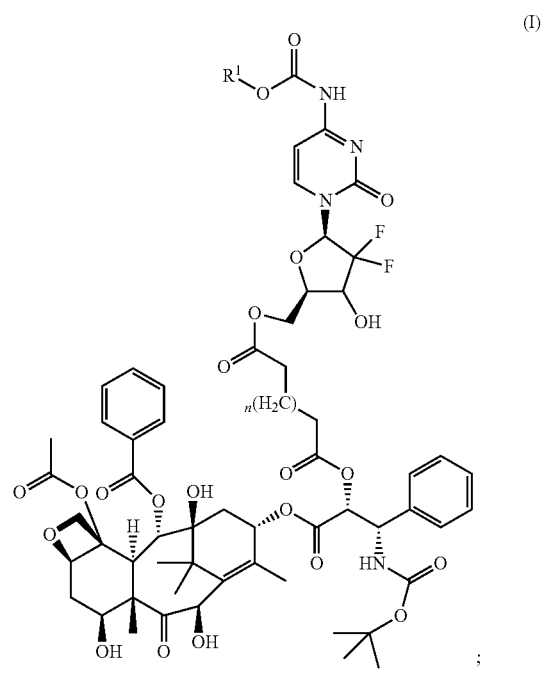

wherein, $R^1$ is $C_1$-$C_6$ alkyl or substituted alkyl; and n is 0-6.

2. The taxane compound according to claim 1, wherein, in formula (I), $R^1$ is ethyl, n-butyl or n-hexyl; and n is 0-2.

3. The taxane compound according to claim 2, wherein, in formula (I), $R^1$ is n-butyl; and n is 1.

4. A method for preparing a taxane compound, comprising:

S1: protecting two hydroxyl groups in gemcitabine; conducting a condensation reaction between the protected gemcitabine and alkyl chloroformate to obtain a first compound; and removing two hydroxy protecting groups of the first compound to obtain an intermediate G1;

S2: protecting a first hydroxyl group of two hydroxyl groups of the intermediate G1 prepared by step S1, then protecting a second hydroxyl group of the two hydroxyl groups to obtain a second compound; and removing, from the second compound, a hydroxyl protecting group corresponding to the first hydroxyl group of the intermediate G1 to obtain an intermediate G2;

S3: reacting 7,10-di-troc-docetaxel with dianhydride to obtain an intermediate D1;

S4: conducting a condensation reaction between the intermediate D1 prepared by step S3 and the intermediate G2 prepared by step S2 to obtain an intermediate D2; and S5: subjecting the intermediate D2 prepared by step S4 to hydroxyl deprotection to obtain a target product, the target product comprising the taxane compound having a structure as shown in formula (I):

(I)

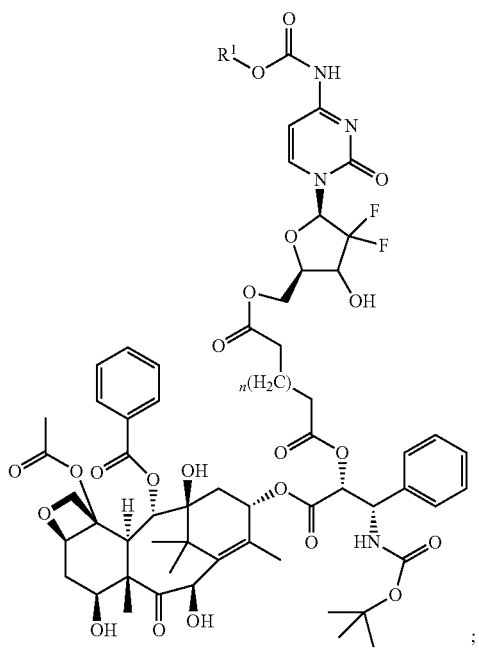

wherein, $R^1$ is $C_1$-$C_6$ alkyl or substituted alkyl; and n is 0-6.

5. The method for preparing the taxane compound according to claim 4, wherein, the alkyl chloroformate in step S1 is n-butyl chloroformate.

6. The method for preparing the taxane compound according to claim 4, wherein, the dianhydride in step S3 is glutaric anhydride.

7. The method for preparing the taxane compound according to claim 4, wherein, a hydroxyl protecting agent used in step S1 is hexamethyldisilazane;

a protecting agent used for protection of the first hydroxyl group in the step S2 is tert-butyldimethylchlorosilane, and a protecting agent used for protection of the second hydroxyl group in Step S2 is 2,2,2-trichloroethyl chloroformate.

8. A method of inhibiting a tumor, comprising: administering to a subject with a therapeutically effective amount of a taxane compound having a structure as shown in formula (I):

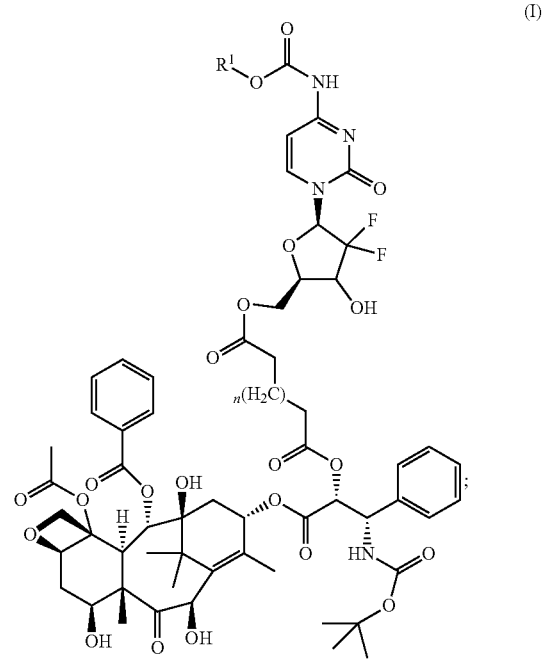

wherein, $R^1$ is $C_1$-$C_6$ alkyl or substituted alkyl; and n is 0-6.

9. The method according to claim 8, wherein, the tumor comprises at least one of: colon cancer, rectal cancer, gastric cancer, lung cancer, breast cancer, prostate cancer, pancreatic cancer, liver cancer, esophageal cancer, brain tumor, ovarian cancer, uterine cancer, kidney cancer, head and neck cancer, skin cancer, bladder cancer, vulvar cancer, testicular tumor, villus cancer, germ cell tumor, malignant lymphoma, leukemia, or multiple myeloma.

10. The method according to claim 8, wherein, the tumor comprises at least one of: colon cancer, rectal cancer, gastric cancer, lung cancer, pancreatic cancer, liver cancer, ovarian cancer, kidney cancer, malignant lymphoma, breast cancer, or leukemia.

* * * * *